United States Patent [19]

Nash

[11] Patent Number: 5,107,448
[45] Date of Patent: Apr. 21, 1992

[54] APPARATUS AND METHOD FOR DETERMINING COEFFICIENTS OF FRICTION

[75] Inventor: Patrick L. Nash, San Antonio, Tex.

[73] Assignee: 501 Board of Regents, The University of Texas System, Austin, Tex.

[21] Appl. No.: 654,934

[22] Filed: Feb. 13, 1991

[51] Int. Cl.⁵ .......................................... G01N 19/02
[52] U.S. Cl. .......................................... 364/556; 73/9
[58] Field of Search ..................... 73/9; 364/550, 556, 364/524, 525, 506

[56] References Cited

U.S. PATENT DOCUMENTS

| | | | |
|---|---|---|---|
| 2,539,578 | 1/1951 | Headley | 73/9 X |
| 4,051,713 | 10/1977 | Bao et al. | |
| 4,098,111 | 7/1978 | Hardmark et al. | 364/426.01 |
| 4,212,063 | 7/1980 | Hardmark | 364/426.01 |
| 4,387,587 | 6/1983 | Faulconer | 73/9 |
| 4,490,802 | 12/1984 | Miller | 364/567 |
| 4,594,878 | 6/1986 | Abe et al. | 73/9 |
| 4,745,464 | 5/1988 | Tennes et al. | 364/566 |
| 4,813,266 | 3/1989 | Nash | 73/9 |

FOREIGN PATENT DOCUMENTS 0153088 12/1979 Japan .
0838527 6/1981 U.S.S.R. .

OTHER PUBLICATIONS

American Society for Testing and Materials, "Standard Test Method for Static Coefficient of Friction of Polish-Coated Floor Surfaces as Measured by the James Machine," Designation D2047-82, May 1982.
Stephen J. Rosen, J. D., Ph.D., The Slipe and Fall Handbook, Chapter Two, "Slippery Surface Falls," pp. 4-28, 1983, Hanrow Press, Columbia, Md., 21044.

Primary Examiner—Parshotam S. Lall
Assistant Examiner—S. A. Melnick
Attorney, Agent, or Firm—Arnold, White & Durkee

[57] ABSTRACT

A microprocessor or computer controlled interactive apparatus to compute coefficients of static and kinetic friction for a test surface using acceleration data of a weighted test block sliding over a test surface. The transient action of the block is damped linear harmonic and is generated by a microprocessor-controlled stepper motor and micrometer connected to the block with two springs. The apparatus provides an accessible graphical display of the recorded acceleration data which comprises a series of relative time values and associated block acceleration values. A movable cursor permits the user to interactively select the point on the surface for which the coefficient of kinetic friction is to be computed. The computed coefficient is then displayed on the graphics display device with the acceleration plot. The cursor may then be redisplayed and moved horizontally with respect to the graphical plot of the acceleration data so that another coefficient of kinetic friction may be computed and displayed for a different selected point. The coefficient of static friction is determined by the amount of elongation of the spring required before the test block breaks free of the static friction and slides over the surface.

13 Claims, 1 Drawing Sheet

APPARATUS AND METHOD FOR DETERMINING COEFFICIENTS OF FRICTION

BACKGROUND OF THE INVENTION

The present invention relates to an apparatus and method for determining coefficients of kinetic and static friction. More specifically, the invention relates to a frictionometer that is either microprocessor-controlled or comprises a plug-in board for an IBM-PC/AT/PS2 computer or compatible.

Two bodies in contact experience mutual frictional forces. The force of kinetic friction operates when the body surfaces are moving relative to one another, while the force of static friction acts on bodies which are stationary with respect to each other. A block at rest on a surface may be placed in motion by applying a force to the block to overcome the static friction which keeps the block at rest. The maximum force of static friction will be the same as the smallest force necessary to start the block in motion. Once motion has started, this same amount of force produces an accelerated motion on the block since the frictional forces acting between the relatively moving surfaces usually are lower than static forces. A smaller applied force than that necessary to start a body in motion may keep the block in uniform motion without acceleration if the resultant force on the block is zero. This small applied force is equal in magnitude but opposite in direction to the force of kinetic friction which is the resisting force between two relatively moving surfaces when that movement is occurring without interruption.

The coefficients of friction provide an indication of the degree of slipperiness between the two contacting surfaces. The coefficient of static friction is computed as the ratio of the magnitude of the maximum force of static friction to the magnitude of the normal force. The normal force is that force which a body exerts on the surface on which the body rests. For a block resting on a horizontal table or sliding along it, the normal force is equal in magnitude to the weight of the block. The coefficient of kinetic friction is computed as a ratio of the magnitude of the force of kinetic friction to the magnitude of the normal force. Generally, the coefficients of friction are values less than one, and generally the coefficient of static friction exceeds the coefficient of kinetic friction.

There is a need in many circumstances to determine a surface's degree of slipperiness. Typically in the building construction industry, contractors are interested in knowing whether surfaces on which people are to walk are safe. Also, situations involving slip and fall accidents may require test analysis to determine whether the surface on which an individual fell could be considered dangerous. Manufacturers of floor polishes are also interested in safety testing surfaces coated with floor polishes being considered for marketing.

The results of slipperiness tests for surfaces are compared with established standards to determine if the surface is dangerous. The National Bureau of Standards established in 1984 a standard for the kinetic coefficient of friction. Research paper RP1879 reported that a slippery condition existed for a surface being tested if the coefficient of kinetic friction was less than 0.40.

The American Society of Testing and Materials established a standard that a static coefficient of friction of 0.50 or above is considered safe for a dry walkway surface. This standard is described in ASTM Standard D 2147-75. Various publications by the National Bureau of Standards recognize this 0.50 standard, and it is reported that the Underwriters Laboratories adopted this as an industry standard.

Generally, the "anti-slip" coefficient (i.e., the coefficient of static friction) values have these meanings.

| Coefficient | Condition |
| --- | --- |
| .60 or above | very safe |
| .50 to .59 | relatively safe |
| .40 to .49 | dangerous |
| .35 to .39 | very dangerous |
| .00 to .34 | unusually dangerous |

A value below 0.50 means that the surface may be considered possibly dangerous to walk on. The higher value indicating safety for static coefficients is valid since test results usually are higher for static than for kinetic values obtained during tests of dry surface conditions.

Several known methods and apparatus have been used to determine the coefficients of friction of a surface. Some have provided information to determine the static coefficient, while others provided information to determine the kinetic coefficient. Since the concern primarily has involved the slipperiness of walkway and walking surfaces, these various devices have used a standard known surface to rest or slide on the surface to be tested. This standard surface has been a flat sanded smooth strip of shoe sole leather.

One such device to measure the coefficient of kinetic friction was developed during the 1940s and employed a pendulum. A strip of shoe leather was attached to the bottom of a weighted block rigidly suspended from a pivot point. A pointer extending from the pivot was attached to the pendulum. The block was raised arcuately to a predetermined height and released. The block swung along an arc towards and over the surface to be tested. After the block slid across the test surface, it continued its arcuate swing upward. The pointer moved upwardly with the block over an arcuately shaped gauge. The coefficient of kinetic friction could be computed using information from the gauge or from knowing the difference between the starting height and the height the block reached in its arcuate swing. This device, however, was not reliable because a portion of the energy was absorbed when the block struck the test surface at the bottom of the pendulum swing. Thus, the block having the shoe leather had to be carefully positioned over the test surface. Also friction created by the pendulum moving the pointer needle affected the results.

A second method used a machine having an articulated strut. A weight was pivotally connected to the upper end of a vertically disposed strut. The bottom of the strut was pivotally connected to a block which had a bottom lining of the test shoe leather. The leather rested on the surface to be tested. An increasing lateral force was applied to the block by rotating the strut until a slip of the block occurred. The coefficient of static friction could then be determined by finding the ratio of the lateral force to the known vertical force imposed by the weight at the upper end of the strut.

A third type of machine which measures the coefficient of friction involved dragging a block over the test surface. The block had a known weight and the bottom surface was lined with the test shoe leather. A force meter connected to the block measured the lateral pull necessary to begin movement of the block. That measurement permitted determination of the static coefficient of friction. Continued pulling of the force meter kept the block in motion and sliding across the test surface. The amount of force necessary to keep the block in motion permitted determination of the coefficient of kinetic friction.

These various devices, however, have limitations. One problem is that the different types of devices have yielded different results for the same surface. To properly evaluate the test results, one must be familiar with the type of equipment used and the effect on test results which arise from the various mechanical linkages involved in the apparatus.

Calibration of these testing machines is critical as well. Present test machines are generally difficult to calibrate against a national standard because of their inherent inaccuracies. Calibration involves using the machine on a surface, usually tile, having a known coefficient of friction.

Known types of friction meters also have had problems with accuracy and reproducibility of measurements and reliability of test results. For instance, in determining the coefficient of static friction, uncertainties arise when attempting to read the force meter at the instant the test block breaks free. It is also time consuming to set up and carry out the number of tests necessary to provide confidence in the test results. It is likely that insufficient data will be collected to obtain a suitable average for a friction coefficient. A large number of tests further may alter the characteristics of the surface being tested. Other errors are introduced when the coefficient of kinetic friction is measured. Traditional slip meters such as the drag type machine require pulling a block at a constant speed, since under ideal conditions the dynamic friction force equals the tension on the pulling string. This approach leads to results that are reliable to only 10 or 15 percent, and are difficult to reproduce by other observers. Also, the meter must be pulled in a straight line or additional acceleration forces will be encountered.

U.S. Pat. No. 4,387,587 issued to Faulconer describes an apparatus and processing methodology for acquiring the deceleration data of a motor vehicle which is skidding over a road surface to a stop. The device mounts to a car and in operation acquires data that may be used to determine the length of the skid and the kinetic coefficient of friction between the road surface and the skidding car.

The test apparatus described in the Faulconer reference includes an accelerator which mounts to the car for sensing the deceleration of the car during a skid. (Since the car is slowing, the acceleration is negative and decreasing, and may be referred to as deceleration.) An analog signal proportional to the declaration is generated at periodic intervals. This signal is converted to a digital value, i.e., digitized, and communicated to a microprocessor. The digitized value is stored together with an associated time value, and is subsequently used in computing the kinetic coefficient of friction, as well as computing other parameters related to the skidding of the car. Faulconer states that the values of acceleration and time may be recorded magnetically by a suitable recorder for computer processing at a later time, and that the data may be displayed on an x-y coordinate graph mechanism.

U.S. Pat. No. 4,813,266 issued to Nash (which is incorporated herein by reference) describes an apparatus and methodology for computing the coefficients of static and kinetic friction for a test surface using deceleration data of a weighted block sliding to rest on a test surface. By striking the test block with a hammer or similar device, the test block is set in motion. An accelerometer measures the deceleration of the block, and the deceleration data is then used to calculate the coefficients of friction.

SUMMARY OF THE INVENTION

The present invention provides a simple and reliable way to determine the coefficients of static and kinetic friction at a specific place on a test surface. It provides an interactive means to focus attention on the specific portion of the surface for which the coefficient is to be computed. Thus, the coefficient of friction may be determined at a localized point.

The frictionometer of the present invention records the transient acceleration of a test block as it slides over the surface to be tested. The transient motion of the block is damped linear harmonic and is generated by the microprocessor-controlled action of springs. The bottom surface of the test block is made from a sample of a standard material specified by the American Society of Testing and Materials to be used in friction measurements. Analysis of the time history of the transient motion of the test block as it moves over the surface under test yields the coefficient of kinetic friction. The coefficient of static friction between the standard material and the surface under test is determined by the amount of elongation of the spring required before the test block breaks free of the static friction and slides over the surface.

The present invention provides an interactive microprocessor or computer controlled apparatus which may be used to acquire data reflecting the slipperiness for a floor surface by using a weighted test block having a bottom surface of a standard test material. The frictionometer according to the invention, being portable, may be used directly in grocery stores, factories or other slip and fall locations. It may also be used in a test lab for testing a variety of surfaces. The present invention provides a significant level of reliability for determining the coefficients of friction at a particular location or surface area. The test performed by the apparatus may be replicated relatively easily and quickly to provide a confidence level for the results. Further, the technician operating the apparatus according to the present invention may select a specific point on the test surface for which the coefficients of friction are to be determined.

The preferred embodiment of the present invention provides a portable device to acquire, store, and analyze digitized data representing the acceleration (positive and negative) of a test block skidding across a test surface. This apparatus includes a test block, a standard leather, an accelerometer, two springs, a slider arm, a slider arm guide, a stepper motor, an analog to digital converter, a microprocessor, a keyboard, and a graphics display device. The microprocessor uses a computer program to operate the apparatus, a random access memory in which to store the acceleration data, and a keyboard to permit communication with the microprocessor. Once the apparatus is activated by the stepper motor, the microprocessor receives and records acceleration data related to movement of the block on the surface. This movement (or nonmovement) is analyzed and a plot of the acceleration data is shown on the graphics display device. Using the recorded data, the coefficient of friction for the surface may be determined. The coefficient of static friction for the starting location (on which the block initially rests) is computed. The coefficient of kinetic friction for each point over which the block slides is available. The average of the coefficient of kinetic friction for the whole of the motion is computed.

DETAILED DESCRIPTION OF PREFERRED EMBODIMENT

Figure 1:
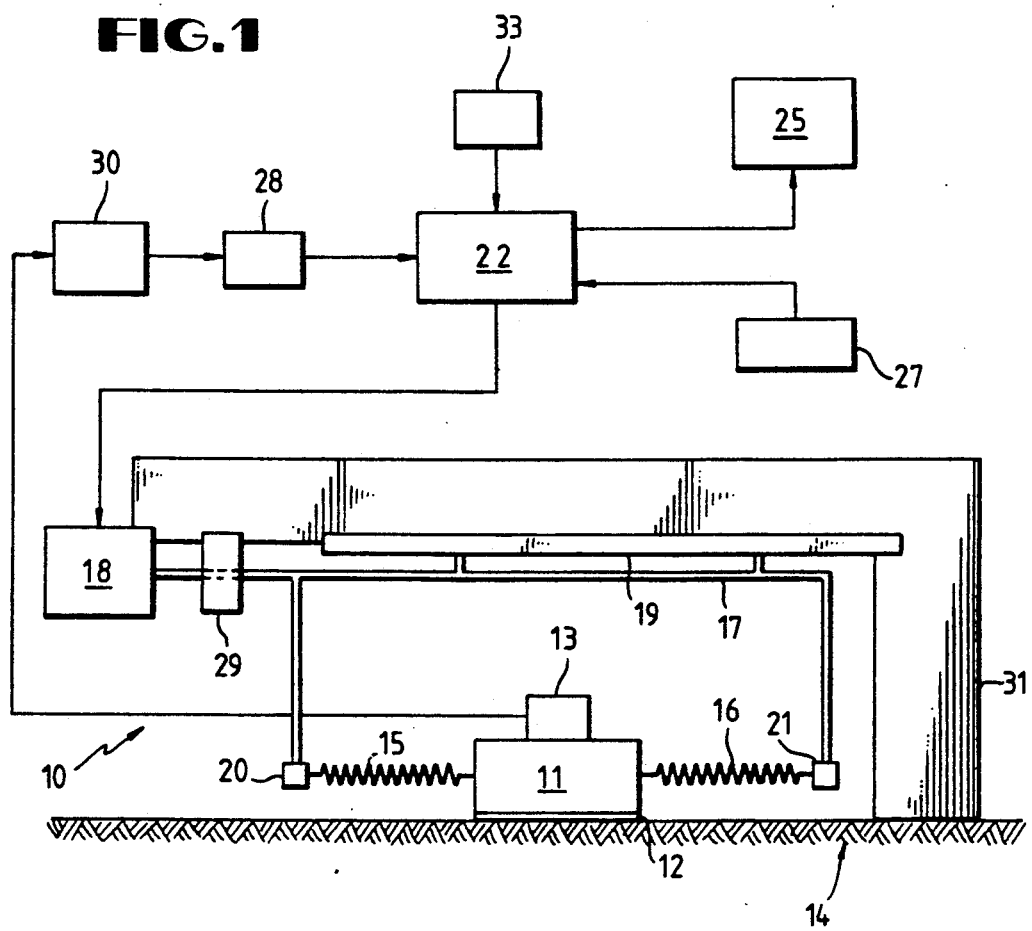
FIG. 1 is a schematic diagram of the apparatus according to the present invention.

With reference to FIG. 1, the apparatus 10 of the present invention includes a test block 11 having a known weight. Attached to the bottom of the block 11 is a strip of standard leather 12. An accelerometer 13 is also affixed to the block 11. The test block 11 rests on a surface to be tested 14.

A spring 15 is attached at its first end to one end of test block 11, and spring 16 is attached at its first end to the other end of test block 11. Spring 15 is slightly elongated and attached at its second end to one end of rigid slider arm 17. This end is designated as end 20. Spring 16 is also slightly elongated and attached at its second end to the other end of rigid slider arm 17, designated end 21. The rigid slider arm 17 is attached to a slider arm guide 19, to a micrometer 29, and to a microprocessor controlled stepper motor 18. The slider arm guide 19 supports the slider arm 17. The slider arm guide 19 is attached to a large stabilizing block 31 which supports the guide 19, the stepper motor 18, and the micrometer 29.

A microprocessor 22 communicates with a display device 25 and a data input device 27 which includes a keyboard and perhaps a mouse. The microprocessor 22 includes or interfaces with (i.e., connects to and communicates with) appropriate read only memory, random access memory and a communications bus to transmit information between an analog to digital converter 28, data input device 27, the display device 25 and the stepper motor 18. Wires or leads connect the accelerometer 13 to the analog to digital converter 28 through a signal conditioner 30. The apparatus also includes a power supply 33.

The components of the present invention may be packaged in a portable container so that the coefficient of friction test apparatus, or frictionometer, may be conveniently carried to the surface location to be tested, e.g., the supermarket floor of a slip and fall accident site.

To operate the frictionometer, the strip of standard leather 12 which meets national test standards is secured to the bottom surface of the test block 11. The standard test material is shoe sole leather which is prepared by sanding the leather to a flat, smooth surface. Federal test method 7121 calls for the use of shoe leather which meets federal specification KK-L-165 leather.

The coefficient of static friction is obtained by using the following method.

The identical springs 15 and 16 of unstretched length LS (LS1 = unstretched length of spring 15 and LS2 = unstretched length of spring 16) are attached to opposite endfaces of the test block 11 of length LB, which has a strip of standard leather 12 on its bottom face. The two springs are stretched and connected to the ends of shallow U-shaped rigid slider arm 17. The distance from one end of the rigid metal bar to the other is LBar. In the preferred embodiment LBar is approximately equal to 3 LS plus LB (about 18" total), the additional factor of LS arising from the extension of the springs from their undeformed lengths. The slider arm 17 acts by moving along the axis of the test block 11 and can extend one spring while shortening the other. The rigid slider arm 17 slides over ball bearings in a guide 19 which is in turn mounted to a large block 31 for stability. A stepper motor 18 turns a micrometer 29, which moves the slider arm 17 forward and backward under the control of microprocessor 22.

The force on the test block 11 due to the springs 15, 16 may be derived from the following considerations. Let the initial position of end 20 of the slider arm 17 be at the origin of coordinates and the center of mass of the test block 11 be at LBar/2 on the x-axis when the apparatus is in its equilibrium configuration (equal tensions in the two springs 15 and 16). Assume that the stepper motor 18 advances the slider arm 17 a distance D along the x-axis and that the center of mass of block 11 moves to X (X = LBar/2 corresponds to no movement of the block 11). If K1 is the spring constant of the spring 15 connecting test block 11 and end 20 of the slider arm 17, and K2 is the spring constant of the spring 16 on the other side of test block 11, then the force, FS, on the test block 11 due to springs 15 and 16 is:

$$FS = K2\left[ D + LBar - \left(\frac{X + LB}{2}\right) - LS2 \right] - K1\left[ \left(\frac{X - LB}{2}\right) - D - LS1 \right].$$

In practice K1 = K2 = K and LS1 = LS2 so that:

$$FS = 2K\left( -X + D + \frac{LBar}{2} \right) = -2Kx,$$

where $$x = X - D - \frac{LBar}{2}.$$

If FS is non-zero and test block 11 is at rest, then there is also a static frictional force acting on the test block 11. The force of static friction is equal in magnitude to FS, but directed along the negative x-axis. Let SMg be its maximum value, where S is the coefficient of static friction, M is the mass of the test block 11 and g = acceleration due to gravity. In order to measure this force an accelerometer 13 is attached to the test block 11; its voltage output is processed by the analog to digital converter 28 and the microprocessor 22. The microprocessor 22 commands the stepper motor 18 to advance the slider arm 17 while it continuously monitors the acceleration signals sent from accelerometer 13 attached to test block 11. When the force due to the springs exceeds the maximum force of static friction, the test block 11 breaks free. The accelerometer 13 continuously sends a signal proportional to the block's acceleration to the analog to digital converter 28. The microprocessor 22, which is interfaced with the analog to digital converter 28, monitors this acceleration. The microprocessor 22 stops the stepper motor 18 in less than about 0.05 milliseconds after the initial acceleration has been detected. The microprocessor 22 keeps track of the number of steps taken by the stepper motor 18 in advancing the micrometer 29, and from this computes D (the distance the springs are deformed). In the preferred embodiment, one step of the stepper motor 18 advances the micrometer 29, and hence the slider arm 17, 0.0192 millimeters. Accordingly, just before the test block 11 breaks free, its acceleration A is zero, $$X = \frac{LBar}{2};$$

by Newton's Second Law of Motion we know that:

$$A = 0 = \frac{FS}{M} - Sg = 2KD - Sg,$$

from which we deduce that:

$$S = 2\frac{KD}{g}. \tag{1}$$

In order to obtain the coefficient of kinetic friction, the microprocessor-controlled frictionometer 10 advances the slider arm 17 until the test block 11 breaks free of the force of static friction and begins sliding under the influence of the kinetic friction force and the force of the springs, as described above for the case of static friction. The microprocessor 22 then locks the slider arm 17, preventing its further motion. Locking is in fact automatic. If the micrometer 29 does not turn, then the slider arm 17 does not move. The microprocessor 22 digitizes and stores in memory the acceleration of the test block 11 from the time just before the block's first move until it comes to rest. The stepper motor 18 is rigidly attached to the large stabilizing block 31, as is the micrometer 29.

In the preferred embodiment, 8192 values of the acceleration are measured and stored in memory at a rate of 20,000 per second, newer values overwriting old values as the 8192 WORD buffer is (re)filled. A complete time history of the acceleration is obtained by programming the microprocessor 22 to turn off digitization and storage of the signal after 7680 values have been acquired once the microprocessor 22 has stopped the stepper motor 18. The 512 (8192−7680) values not overwritten comprise a record of the acceleration just before the block 11 breaks free. Assuming that the test block 11 is sliding in the positive direction along the x-axis, Newton's Second Law yields $MA = FS - \mu Mg$ where $\mu$ is the coefficient of kinetic friction; hence:

$$\mu = \frac{FS}{Mg} - \frac{A}{g} = -\left(\frac{2K}{Mg}\right)x - \frac{A}{g}. \tag{2}$$

(The value of x for a time t is obtained by numerically integrating acceleration to get velocity as a function of time, then numerically integrating velocity to obtain x.) The average value of $\mu$ for the trial may be obtained by multiplying Eq. (2) by velocity and integrating with respect to time over the duration of the motion. If Z represents the distance along the x-axis that the test block 11 slides, then this yields:

$$\mu_{average} = \mu_s\left(1 - \frac{Z}{2D}\right). \tag{3}$$

Z is obtained by numerical integration of the acceleration.

Figure 2:
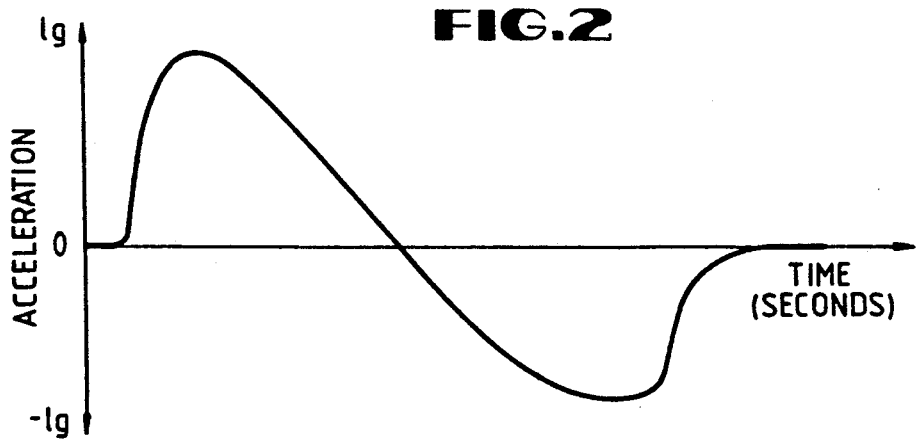
FIG. 2 is a typical plot of acceleration versus time for a test block sliding over a surface in response to the force applied by the slider arms and springs.

Apparatus according to the invention provides to a user an accessible graphical display of recorded acceleration data for a block 11 having an industry standard leather surface 12 skidding across the test surface 14. The data comprise a series of time values and associated block acceleration values. The data are collected and stored in the memory of the microprocessor 22 operating under control of a computer program. The accessible graphical display 25 permits the engineer or other individual testing surfaces to select the point on the surface 14 for which the coefficient of friction is to be computed. The selection capability is accomplished by graphing on the display device 25, such as a liquid crystal output device, a plot of the block's acceleration versus time. FIG. 2 shows a typical plot of acceleration versus time for test block 11 sliding over a surface 14 in response to the force applied by the stepper motor 18. Once the recorded data are displayed, the computer program operating the apparatus may be instructed to display on the graph a cursor. Using data input device 27 commands, the cursor may be moved back and forth on the plot. A vertical cursor intersects the curve of graphed data, and the user may use that cursor to spot or select a time point on the graph at which the coefficient of friction is to be computed.

In one preferred embodiment, moving the cursor to the selected time point commands the microprocessor 22 to select the point where the cursor is located. The computer program locates that selected point in the recorded acceleration data. A number of data points following the selected data point are then used to computer the average coefficient of friction. Preferably, the number of data points used in computing the average acceleration will be about 16, although this number may be varied depending on the accuracy desired and the number of data points recorded per second as the test block 11 skids on the test surface 14. In an alternate embodiment, the computer program uses the selected point as the middle and takes about the same number of data values on either side of the selected point. In another alternative embodiment, the moving of the cursor and the selecting of a data point may be separate steps having separate keyboard commands.

Once the coefficient of friction is computed, its value is preferably displayed on the liquid crystal output device 42 next to the plotted curve. The user may then rerun the test, or redisplay the cursor to select another data point at which to compute the coefficient of friction.

The theoretical underpinnings of the frictionometer are expressed by the following equations. Consider the test block 11 of the frictionometer 10 positioned on a surface 14 whose material properties are under investigation. The test block 11 has mass M. Let X be the x-coordinate of the center of mass of the test block 11, $$V = \frac{dX}{dt}$$

be the x-component of its velocity and $$A = \frac{dV}{dt} = \frac{d^2X}{dt^2}$$

the x-component of its acceleration. The y-component of the test block's 11 velocity and the y-component of the acceleration are identically zero and therefore need not be explicitly considered further. Two forces act on the test block 11 along the x-axis, the force $F_{springs}$ due to the two springs 15, 16 attached to opposite faces of the text block and the force of friction, $F_{friction}$. Newton's Second Law of Dynamics provides that $$MA = F_{springs} + F_{friction}. \quad (4)$$

Here $F_{springs} = FS = -2Kx$ and $$F_{friction} \leq \begin{cases} -\mu_{static}Mg & \text{if } V = 0 \text{ and } F_{springs} > 0 \\ \mu_{static}Mg & \text{if } V = 0 \text{ and } F_{springs} < 0 \end{cases}$$

in the static case and $$F_{friction} = \begin{cases} -\mu_{kinetic}Mg & \text{if } V > 0 \\ \mu_{kinetic}Mg & \text{if } V < 0 \end{cases}$$

for the dynamic problem.

The motion of the test block 11 for the special case of zero frictional force is periodic oscillation about the equilibrium point. The amplitude of the oscillation does not change with time. This is called linear (or simple) harmonic motion. When the force of friction is not zero (the usual case) the motion is still periodic but the amplitude of oscillation decreases to zero with time. This is called damped harmonic motion. If the frictional force is strong enough (the case for the frictionometer), then the test block 11 only completes a small fraction of an oscillation before coming to rest.

An accelerometer 13 rigidly attached to the test block 11 allows the microprocessor 22 to "continuously" monitor the acceleration of the test block 11. Actual measurements of the acceleration are made approximately every 1/20,000 second. This sampling rate is programmable and can be adjusted as required.

The amplified voltage output from the accelerometer 13 is fed through a signal conditioner 30 to the analog-to-digital converter 28. When the test block 11 breaks free into motion, the voltage output from the accelerometer 13 rapidly increases from zero to a positive value. As soon as it exceeds a small preset level a voltage comparator changes state (going from LOW to HIGH). This voltage change triggers a counter to count down from 8192−512=7680 to zero. At the terminal count the counter (an Advanced Micro Devices Am9513A) disables further storing in memory of the digitized test block 11 accelerations. Thus, a complete record of the acceleration of test block 11 is stored in memory, from a time just before test block 11 breaks free into motion until a short time after test block 11 comes to rest. The programmable sampling rate is adjusted so that test block 11 acceleration is digitized and stored in RAM for the duration of the motion. For example, if the surface 14 under test is especially slippery so that test block 11 slides for a time longer than usual, then the frictionometer operator decreases the sampling rate so that a longer period of time is represented by the data stored in the 8192 memory locations. (Alternatively, one could increase the size of RAM.)

The programmable Am9513A counter/timer is also used to generate the sampling rate.

The velocity of test block 11 at time t is related to the initial velocity V(0) at initial time t=0 by $$V(t) = V(0) + \int_0^t A(t_1)dt_1 \quad (5)$$
$$= \int_0^t A(t_1)dt_1,$$

since the initial velocity of the block 11 is zero.

The change in position $\Delta X(t)$ of the center of mass of test block 11 is given by $\Delta X = X(t) - X(0)$, where t is the elapsed time from the instant that test block 11 breaks the bond of static friction and starts to move (we shall=refer to this time as the time of the trigger). $\Delta X$ is given by $$\Delta X(t) = \int_0^t V(t')dt' \quad (6)$$
$$= \int_0^t \int_0^{t'} A(t_1)dt_1 dt'$$
$$= \int_0^t (t - t')A(t')dt',$$

where in the last equation the order of integration in the double integral has been interchanged and one integration has been performed. Equation (6) has a simple discrete analog which is used to obtain the displacement of the block 11 from its initial position from the measured values of the acceleration. Let $\rho$ = sampling rate ≈20,000 per second, $\delta t = 1/\rho$ = time interval between samples, $t_n = n\delta t$, n=0,1, ... N<8192 be the $n^{th}$ time value since the trigger and $A_n = A(t_n)$. Then $$\Delta X(t_n) = (\delta t)^2 \sum_{i=0}^{n} (n-i)A_i. \quad (7)$$

Using this result and the definition of $$x(t_n) \stackrel{def}{=} x_n = X(t_n) - D - LBar/2 = \Delta X(t_n) - D$$

the coefficient of kinetic friction $\mu_{kinetic}$ at any time $t_n$ can be obtained:

$$\mu_{kinetic}(t_n) = -\frac{2K}{Mg}x_n - \frac{A_n}{g}. \quad (8)$$

To obtain the average value of the coefficient of kinetic friction Equation (8) is multiplied by dx and integrated over the range of motion. If Z denotes the total distance that the test block slides along the x-axis, then $$Z = (\delta t)^2 \sum_{i=0}^{N} (N - i) A_i \qquad (9)$$

where N = #samples − 1 = 8192 − 1. The average of the coefficient of kinetic friction is given by $$\mu_{kinetic} = \mu_{static} \left(1 - \frac{Z}{2D}\right). \qquad (10)$$

This uses the fact that $$\int_{X_0}^{X_{final}} A dx = \int_{0}^{t_{final}} A(t) V(t) dt = \qquad (11)$$

$$\frac{1}{2} V(t_{final})^2 - \frac{1}{2} (V(0))^2 = 0$$

since $V(t_{final}) = 0$ and $V(0) = 0$.

There has been described herein a method and apparatus for acquiring data related to the slipperiness of a test surface 14 and interactively accessing selected data points to compute the coefficients of friction, kinetic and/or static, for the test surface 14. It will be apparent to those skilled in the art who have the benefit of this disclosure that a number of variations may be made to the apparatus and method of the present invention such as the size or weight of the block, the length of the slider arm, substituting rubber bands or elastic straps for the springs, etc. These variations are to be considered within the spirit and scope of the invention which is limited only by the following claims.

What is claimed is:

1. An apparatus for measuring coefficients of friction of a surface, said apparatus comprising:
    a test block having two ends, said block being adapted to rest on a surface to be tested;
    an accelerometer attached to the test block and operable to generate signals correlating to acceleration of the test block along the surface;
    a first spring having two ends, a first end of the first spring being connected to a first end of the test block;
    a second spring having two ends, a first end of the second spring being connected to a second end of the test block;
    means connected to the second ends of the first and second springs for moving the block; and
    means for receiving and recording signals from the accelerometer attached to the block.

2. An apparatus as recited in claim 1 wherein the means for moving the block comprises a generally U-shaped slider arm, said slider arm being connected at a first end to the second end of the first spring and connected at a second end to the second end of the second spring.

3. An apparatus as recited in claim 2 wherein the first and second springs are both in tension when the apparatus is at equilibrium.

4. An apparatus as recited in claim 2 wherein the means for moving the block further comprises a stepper motor and micrometer for moving the slider arm in discrete increments.

5. An apparatus as recited in claim 4 further comprising a slider arm guide to hold the slider arm and direct its movement in a straight line.

6. An apparatus as recited in claim 1 wherein the means for receiving and recording signals comprises a signal conditioner, an analog to digital converter, and a microprocessor.

7. An apparatus as recited in claim 6 wherein the microprocessor also controls the means for moving the block.

8. An apparatus for measuring coefficients of friction of a surface, comprising:
    a test block having two ends, said block being adapted to rest on a surface to be tested;
    a standard leather attached to the bottom of the test block in contact with the surface to be tested;
    an accelerometer attached to the test block and operable to generate signals responsive to acceleration of the test block along the surface;
    a first spring having two ends and connected at a first end to a first end of the test block;
    a second spring having two ends and connected at a first end to a second end of the test block;
    a slider arm having two ends and connected at a first end to a second end of the first spring, the slider arm being connected at a second end to a second end of the second spring, and the slider arm adapted to be slidably connected to a slider arm guide;
    a stepper motor and micrometer adapted to move the slider arm;
    an analog to digital converter adapted to receive analog signals from the signal conditioner which receives signals from the accelerometer and convert the analog signals into digital signals;
    a microprocessor adapted to receive and store the digital signals from the analog to digital converter, the microprocessor also being adapted to control the stepper motor, and being further adapted to calculate the coefficients of friction for the test surface; and
    a data input device adapted to allow the operator of the apparatus to interact with the microprocessor.

9. An apparatus as recited in claim 8, wherein the stepper motor and micrometer combination are capable of moving the slider arm in discrete increments.

10. An apparatus as recited in claim 8, wherein the springs are elongated when connected to the test block and the slider arm.

11. A method of determining coefficients of friction, comprising:
    providing a test block adapted to rest on a surface to be tested, said block being connected at its ends by elongated springs to a slider arm, said test block also having an accelerometer attached thereto;
    moving said slider arm until the test block moves;
    measuring and recording the movement of the slider arm; and
    measuring and recording the acceleration of the test block.

12. A method as recited in claim 11 wherein said moving step comprises moving the slider arm in discrete segments.

13. A method as recited in claim 11 wherein the acceleration from the accelerometer is converted from an analog to a digital signal and is recorded by a microprocessor.

* * * * *